United States Patent
Rousseau et al.

(10) Patent No.: US 6,355,488 B1
(45) Date of Patent: Mar. 12, 2002

(54) METHOD FOR CONTINUOUS OR DISCONTINUOUS AUTOMATIC ANALYZING OF SAMPLES PLACED IN CONTAINERS

(75) Inventors: Alain Rousseau, Paris; Jean-Francois Gelin, Creteil, both of (FR)

(73) Assignee: Diagnostica Stago (FR)

(*) Notice: Subject to any disclaimer, the term of this patent is extended or adjusted under 35 U.S.C. 154(b) by 0 days.

(21) Appl. No.: 09/242,307
(22) PCT Filed: Jun. 11, 1998
(86) PCT No.: PCT/FR98/01223
§ 371 Date: Aug. 12, 1999
§ 102(e) Date: Aug. 12, 1999
(87) PCT Pub. No.: WO98/58261
PCT Pub. Date: Dec. 23, 1998

(30) Foreign Application Priority Data
Jun. 16, 1997 (FR) .............................. 97 07751

(51) Int. Cl.⁷ .................. G01N 35/04; G01N 35/02
(52) U.S. Cl. ................. 436/47; 436/48; 422/65; 422/67
(58) Field of Search ................ 422/65, 67; 436/47, 436/48

(56) References Cited

U.S. PATENT DOCUMENTS

| | | | | |
|---|---|---|---|---|
| 5,972,295 A | * | 10/1999 | Hanawa et al. | 422/65 |
| 5,985,215 A | * | 11/1999 | Sakazume et al. | 422/67 |
| 6,117,683 A | * | 9/2000 | Kodame et al. | 436/47 |

\* cited by examiner

Primary Examiner—Nina Bhat
(74) Attorney, Agent, or Firm—William A. Drucker

(57) ABSTRACT

A method provides for the placing of samples containers inside holders, a first displacement bringing the holders to an zone with access to the blood analyser pipetting area, identifying the containers during this displacement, a second rectilinear displacement through the pipetting zone along a path perpendicular to the first, a third rectilinear displacement bringing the holders to a second zone acceding to the pipetting area a fourth displacement through the pipetting area and bringing the holders to second outlet zone located on the first path and a path bringing the holder, to the first access zone or an evacuating zone. The method is particularly useful for carrying out hemostasis test on centrifuged blood samples.

13 Claims, 2 Drawing Sheets

METHOD FOR CONTINUOUS OR
DISCONTINUOUS AUTOMATIC ANALYZING
OF SAMPLES PLACED IN CONTAINERS

This application claims benefit under 35 U.S.C. 371 of PCT/FR98/01223 filed Jun. 11, 1998.

BACKGROUND OF THE INVENTION

1. Field of the Invention

The present invention concerns a method for continuous or discontinuous automatic analysing of samples placed in containers, such as test tubes.

2. Description of the Prior Art

So as to be analysed, the sample recipients are frequently placed in line in containers or "portoirs", each containing several tubes (usually five) vertically centred inside a longitudinal vertical median plane of the container.

The containers equipped with their samples are then disposed in line on a conveyor passing into an analysis station of an analysis robot where they undergo one after the other the pipetting operations adapted to the analysis to be conducted.

This sequential processing of samples has various drawbacks:

difficulty of restarting a test or additional analysis (it is necessary to manually look for the tube in the already sampled containers), the samples are stored at ambient temperature, which is highly prejudicial to certain unstable parameters, the tube sorting for storing samples in the sample library or delaying tests is extremely difficult, the urgent processing of tubes proves to be difficult owing to the fact that it is necessary to short-circuit the waiting queue.

This is why analysis robots have been suggested, said robots including a pipetting area in which the previously identified sample recipients are disposed according to a matrix distribution. According to two perpendicular co-ordinate axes, an injection and/or sampling head (pipetting head) moves above this pipetting area, the functioning of said head and the movements being controlled by a robot controlled by a processor. It is clear that by means of this disposition, it becomes possible to carry out several analysis processings in parallel and thus restart at any time. The drawback of this solution thus lies in the fact that it does not allow a continuous or semi-continuous loading of the robot: each operating sequence requires a manual loading of the pipetting area with identification of each tube, its location and the type of analysis to be carried out.

These operations, which require the presence of an operator, are relatively long and are unable to guarantee that no error occurs, especially in the identification/tube position relation.

OBJECT OF THE INVENTION

With the aim of eliminating these drawbacks, the invention puts forward a method using an analysis robot of said type in which the sample recipients (such as the tubes), previously disposed in containers, are able to move inside the pipetting area during the phases for analysis, loading and unloading of this pipetting area, as well as the movements of containers inside the latter being carried out automatically.

SUMMARY OF THE INVENTION

So as to obtain this results, the method according to the invention includes an operational cycle comprising at least the following phases:

placing the containers of sample to be analysed inside containers in which the vertically centred containers are placed in line parallel to the longitudinal axis of said containers, a first movement of the containers one after the other along a first rectilinear path so as to bring them to the right of an access zone at the pipetting area, a preferable automatic identification of the recipients during this first movement, a second rectilinear movement along a path perpendicular to the first, during which the containers, placed side by side, are translation-moved and traverse straight through the pipetting area so as to reach an outlet zone situated opposite the access zone, a third rectilinear movement zone along a path parallel to the first during, which the containers are brought one after the other from the first outlet zone to a second inlet zone at the pipetting area, a fourth rectilinear movement along a path parallel to the second during, which the containers, which are again placed side by side parallel to the first path, are translation-moved through the pipetting area so as to reach a second outlet zone situated on the first path, a fifth rectilinear movement along the first path so as to bring the container to the first access zone so as to restart a new cycle or to an evacuation zone of the container.

By means of these dispositions:

during the second path, each container scans a first fraction, such as a first half, of the pipetting area, during the fourth path, each container scans a second fraction, such as the second half, of the pipetting area, during each of these two paths, each recipient moves onto the same column of the matrix of the pipetting area.

Thus, with the aid of relatively simple sensors, it is possible to determine the position of each of the containers, the processor controlling the movements of the pipetting head being able to know at each moment, the position of each recipient in the pipetting area. Therefore, it is possible to carry out samplings or injections of products in any recipient present in the pipetting area according to a function programme of the type of analysis to be carried out, independent of the order in which the recipient has been introduced into the analysis robot.

Of course, the invention also concerns an analysis robot designed to implement the previously described method, this robot introducing on both sides of the pipetting area a first unit comprising two parallel linear conveyors designed in such a way so as to transport the containers in line orientated along the displacement axis of these conveyors, and a second unit including at least two perpendicular linear conveyors to the first two and designed so as to transport the containers, orientated perpendicular to the displacement axis of these two conveyors, into the pipetting area, the conveyors of this second unit opening into the inlet/outlet transfer zones of the two conveyors of the first unit.

The analysis robot could preferably include a device for reading the identification codes inscribed on the cylindrical walls of the tubes contained in the containers, this reading device equipping one of the linear conveyors upstream of said transfer areas of this conveyor.

Similarly, the pipetting area and more generally the inside of the analysis robot could be kept at a suitable temperature for preserving the samples.

BRIEF DESCRIPTION OF THE DRAWINGS

An execution mode of an analysis robot of the invention shall be described hereafter by way of non-restrictive example with reference to the accompanying drawings on which.

DESCRIPTION OF THE PREFERRED EMBODIMENTS

In this example, the purpose of the automatic analysis robot A is to carry out hemostasis tests on centrifuged blood samples contained in tubes T, identification data in the form of a bar code being indicated on the wall of said tubes and concerning, for example, the identity of the person from whom the blood sampling has been taken and the nature of the tests which need to be carried out.

During the process preceding the test execution phase, the blood samplings contained in the sealed tubes T are placed in the container of a centrifugal machine where they are subject to centrifugal action. The tubes can be kept in the containers so as to avoid being handled.

Figure 3:
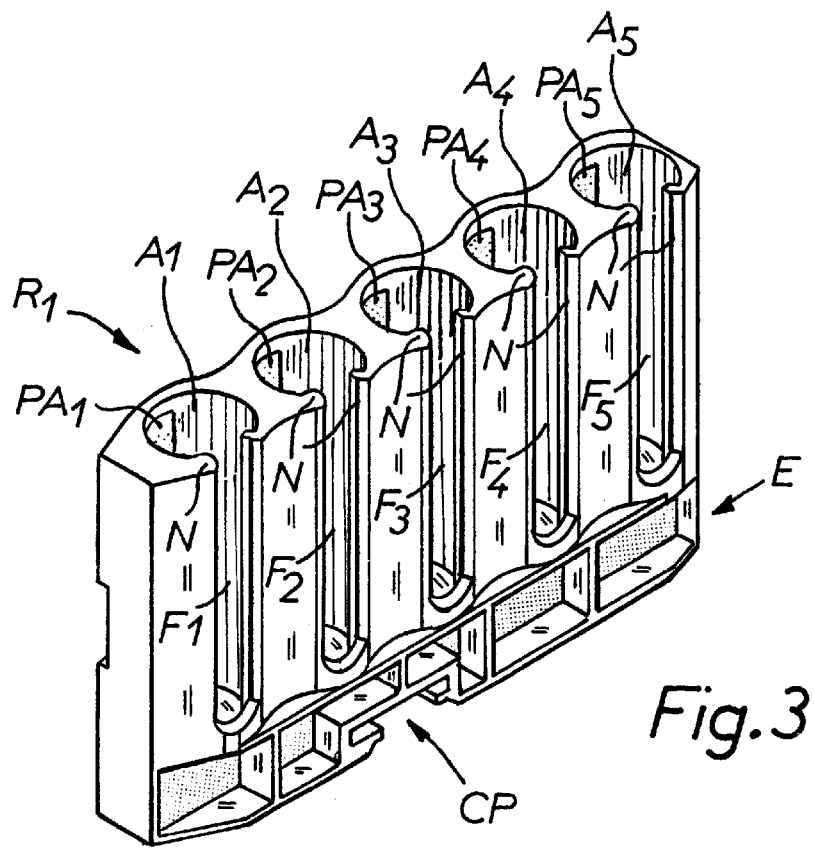
FIG. 3 is a perspective view of a container made specially to allow reading of the sample tubes.

On leaving the centrifugal machine, the tubes are placed in containers R, for example of the type shown on FIG. 3 which contains five tubes T. The containers R are placed in easily transportable baskets and specially designed so as to be placed in a container distributor D which constitutes the access station of the containers at the analysis robot A.

The containers R in these baskets are placed side by side so as to form a line orientated perpendicular to the longitudinal axis of the containers.

Figure 1:
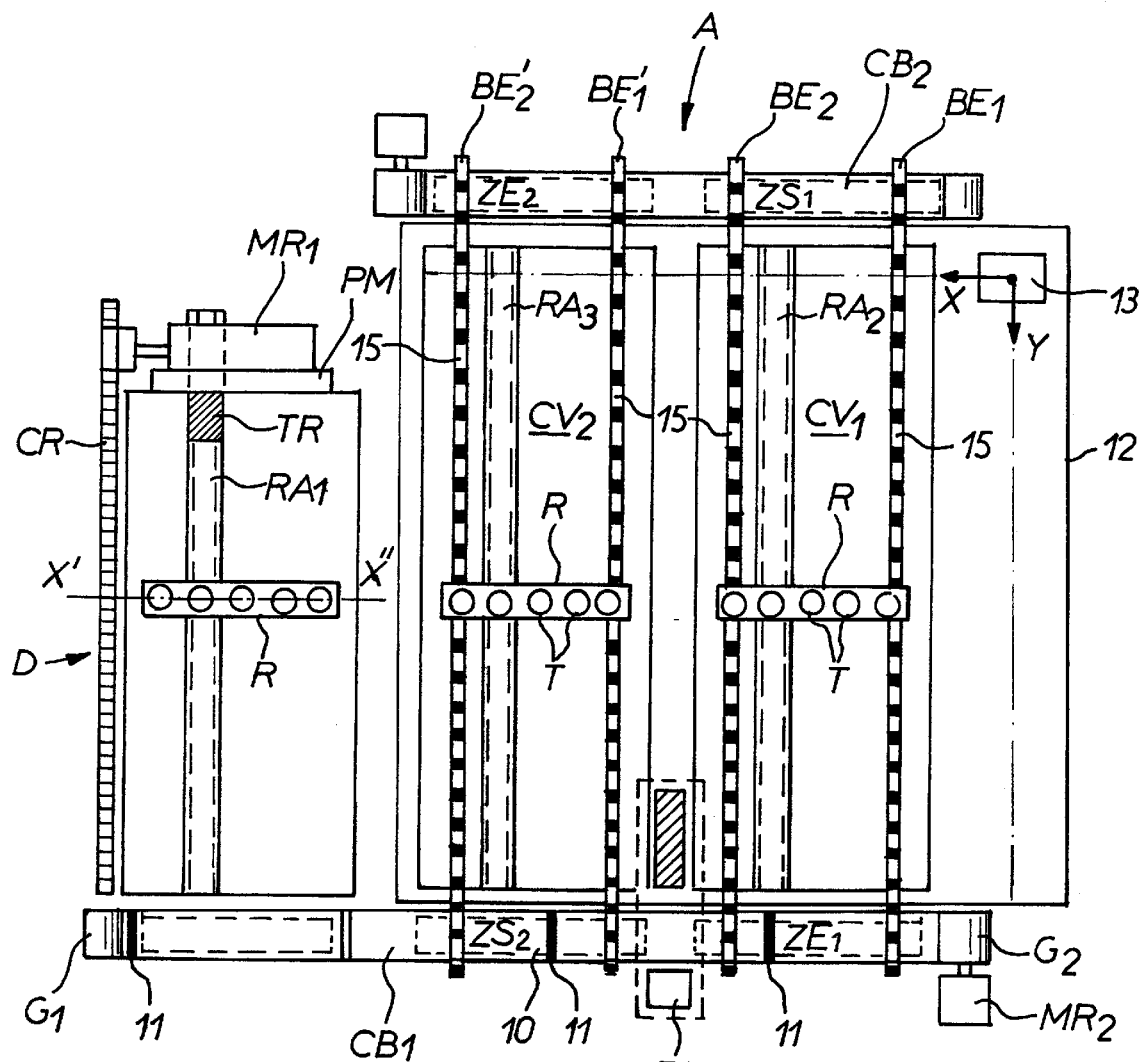
FIG. 1 is a diagrammatic top view of an analysis robot according to the invention.
Figures 4, 5:
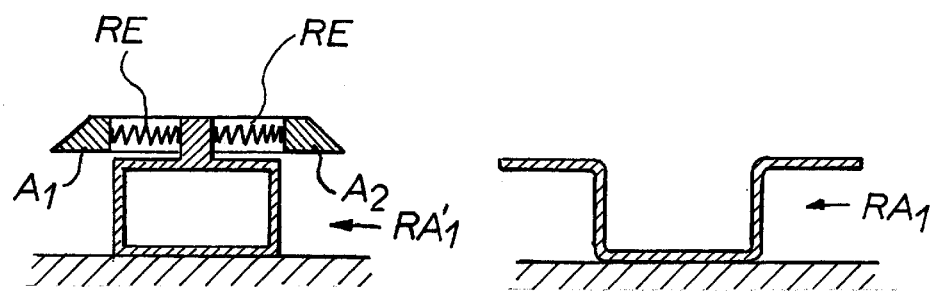
FIG. 4 is a cutaway view of a guiding rail of the containers with a feed section with retractable wings.
FIG. 5 is diagrammatic transverse section of the retractable section.

In fact, inside the basket, the containers R are guided in the direction of the line by an inverted Ω-shaped profiled rail $RA_1$ integral with the bottom of the basket and which is engaged in a transverse prismatic cavity CP with a T-shaped section made in the seat E of the containers R. The placing of the containers R on the rail $RA_1$ can be facilitated by providing at the end of the rail $RA_1$ a section TR in which the lateral wings $A_1$, $A_2$ of the rail $RA_1$ are retractable. This result can be obtained by providing wings with a bevelled edge $A_1$, $A_2$ able to move towards the inside of the rail $RA_1$ and kept in their position by springs RE (FIG. 5).

By means of this disposition, it becomes possible to assemble containers on the rail $RA_1$ by engaging it via the top of the rail section TR at the end of a vertical movement during which the outer edges of the cavity CP come to rest on the bevelled edges of the lateral wings $A_1$, $A_2$ by provoking their retraction. When the wings $A_1$, $A_2$ reach the level of the widest portion of the cavity CP, they spread out under the effect of the springs RE, thus carrying out mounting. The container can then be translation-moved perpendicular to its longitudinal axis X'X" so as to reach the section with fixed wings of the rail $RA_1$. This solution proves to be more ergonomic and simpler than the solution which consisted of attaching the containers R via an end of the rail $RA_1$.

In this example, the container distributor D includes a thrustor PM able to move inside the axis of the basket bottom rail $RA_1$ and whose movements are ensured with the aid of a back-geared motor $MR_1$ which drives a pinion P1 gearing with a rack CR centred parallel to the rail. This thrustor PM is used to move the containers R of the line along the rail $RA_1$ so as to bring the final container R of the line onto the belt conveyor $CB_1$ which feeds the analysis robot. At the time they are moving, the containers R pressed against one another the others remain orientated perpendicular to the rail $RA_1$.

On the other hand, the containers R moved one by one on the conveyor $CB_1$ are orientated along a displacement axis perpendicular to the rail $RA_1$.

The conveyor $CB_1$, with a conventional structure, is formed of an elastomer strip 10 passing onto two rollers $G_1$, $G_2$ with parallel horizontal axes, one roller $G_2$ being driven in rotation by a back-geared motor $MR_2$. The strip 10 includes, on its outer face, notches 11 whose spacing corresponds approximately to the length of one container R.

This strip 10 circulates along a longitudinal edge of a pipetting area 12 of the robot A, successively opposite an outlet zone and an access zone at the pipetting area 12.

The pipetting area 12 having a rectangular shape is intended to receive two lines of containers R placed side by side, above which a conventional pipetting head 13 is able to move along two perpendicular directions X and Y, said head being fitted with means allowing injections and/or samplings to be carried out inside the tubes contained in the containers.

This pipetting area 12 is in fact materialised by areas for the passage of two conveyors $CV_1$, $CV_2$ centred perpendicular to the conveyor $CB_1$ and which extend from the access and outlet zones $ZE_1$ and $ZS_2$.

These conveyors $CV_1$, $CV_2$ each introduce a guiding rail $RA_2$, $RA_3$ at Ω (similar to the basket bottom rail) centred perpendicular to the conveyor $CB_1$ and on which the containers R borne by the conveyor $CB_1$ are engaged via their prismatic cavities CP.

Disposed on both sides of this rail $RA_2$, $RA_3$ are two drive strips $BE_1$, $BE_2$ -$BE'_1$, $BE'_2$ fitted with notches 15 whose step is approximately equal to the thickness of the containers R.

The transfer of the containers R from one conveyor $CV_1$, $CV_2$ to another is ensured either by the belt conveyor $CB_1$, or by a second belt conveyor $CB_2$ which extends along the longitudinal edge of the pipetting area 12, opposite the conveyor $CB_1$.

This conveyor $CB_2$ which has a structure similar to that of the conveyor $CB_1$ passes successively into the outlet zone $ZS_1$ of the conveyor $CV_1$ and then into the inlet zone $ZE_2$ of the conveyor $CV_2$.

This therefore allows a transfer by moving the containers R along their longitudinal axis so that in the access zone $ZE_2$, the container R is located inside the axis of the conveyor $CV_2$. This container R is then driven by the notches of the strips 15 and becomes engaged via its prismatic cavity on the rail $RA_3$ where it is able to slide until it reaches the outlet zone $ZS_2$.

The movements of the containers R in the pipetting area 12 could preferably be made step by step, each step corresponding to the thickness of one container R. In this case, the movements of the containers R by the conveyors $CB_1$, $CB_2$ shall also be carried out step by step in synchronism with the preceding ones.

In this example, the conveyor $CB_1$ is equipped with an automatic tube identification station PI disposed at the level of the joining point between the passage areas of the containers R on the conveyors $CV_1$, $CV_2$. This device shown on FIG. 2 involves the use of containers R including on one side, a perforated lateral face $FL_1$ whose perforations constitute windows F intended to allow the optical reading of identification codes borne by the cylindrical walls of the tubes T, and on the other side, an aperture-shaped orifice OF which extends over the entire length of the lateral face $FL_2$ of the container R.

Figure 2:
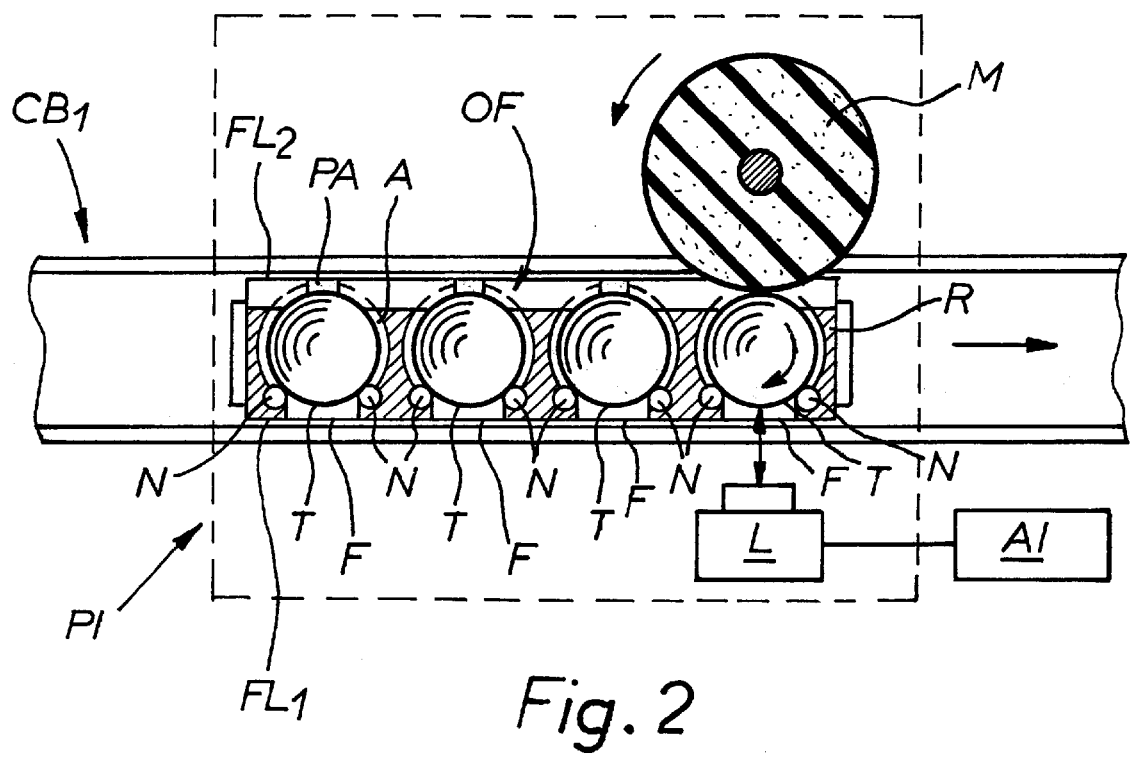
FIG. 2 is a view on larger scale of a device for automatically reading the identification codes inscribed on the sample tubes.

As shown on FIG. 2, the identification station, illustrated by a rectangle with broken lines, includes:

firstly, an optoelectronic reading device L (for example a video camera associated with an image analyser AI) disposed on one side of the conveyor $CB_1$ so as to record the image of the cylindrical wall of each of the tubes T each time the window F enabling this tube T to be seen is located inside the field of the reading device L, and secondly, a drive device consisting of a wheel M made of a resilient material, such as rubber, driven by an electric motor, this wheel M, centred vertically, is disposed at the right of the reading device L, of the other side of the conveyor $CB_1$ so as to be able to be engaged inside the longitudinal orifice OF of the container R so as to successively rest on the cylindrical wall of the tubes T and thus ensure the latter are driven in rotation.

In the example shown on FIG. 3, the container, having a general parallelepiped shape with bevelled vertical edges, includes a seat E fitted with a rib delimiting a transverse prismatic cavity CP with an approximately C shaped or round tail-shaped section and intended to co-operate with a guiding rail $RA_1$, $RA_2$, $RA_3$ with a complementary section, such as a T-shaped section.

The upper portion of the container R includes five vertical cylindrical alveoles $A_1$ to $A_5$ open at the level of the upper face of the container and intended to receive five respective tubes.

On the side of the face $Fl_1$, these alveoles $A_1$ to $A_5$ open towards the outside by means of oblong windows $F_1$ to $F_5$ extending from the upper face of the container up to the level of the seat E.

On the side of the face $FL_2$, the container $R_1$ includes an orifice OF with a rectangular section which extends horizontally to the mid height of the container R, from one of its ends to the other. The depth p of this orifice is provided so that one portion of the wall of the tubes is uncovered and is thus able to co-operate with a rotation drive member of the type of the wheel M shown on FIG. 2.

Moreover, the alveoles $A_1$ to $A_5$ of the container include on both sides of the windows $F_1$ to $F_5$ ribs N on which the tubes preferably tangentially come to rest.

Provided opposite each of the pairings of ribs N is a flexible tongue $PA_1$ to $PA_5$ which extends slightly obliquely into the internal volume of the corresponding alveole $A_1$ to $A_5$ so as to keep the tube applied on the ribs N.

It appears by means of the previously described dispositions, the containers, initially contained in the basket placed in the distributor D, are transferred one by one onto the belt 10 of the conveyor $CB_1$ which transports them successively to the identification station PI where the identification codes borne by the tubes are successively read, then in the access zone $ZE_1$ at the pipetting area 12 in a position according to which the prismatic cavity CP is located exacted inside the axis of the rail $RA_2$.

The container R now positioned in the zone $ZE_1$ is then driven by the notches 15 of the two drive strips $BE_1$, $BE_2$. This driving first of all provokes the engagement of the rail $RA_2$ in the prismatic cavity CP of the container R and then the sliding of the container R along the latter until it reaches the outlet zone $ZS_1$ situated on the conveyor $CB_2$. The passage of the container R inside this zone $ZS_1$ causes it to be dismantled from the rail $RA_2$ and then its driving by the conveyor $CB_2$ as far as the access zone $ZE_2$ where it is positioned so as to be able to be engaged on the rail $RA_3$. The container R is then driven by the conveyor $CV_2$ and slides onto the rail $RA_3$ until it reaches the outlet zone $ZS_2$ where is it disengaged from the rail $RA_3$.

The container R is then driven by the conveyor $CB_1$, either towards the access zone $ZE_1$ to start a new analysis cycle, or towards the distributor D so as to ensure, by means of a process opposing the preceding one, a return of the containers into the previously empty basket, or even towards an unloading zone (not shown).

Of course, the control of the distributor D, of the various conveyors $CB_1$, $CB_2$, $CV_1$, $CV_2$ of the identification station PI and of the analysis robot A (in particular of the pipetting head 13) is ensured by a processor which receives a multiplicity of information originating from position sensors disposed along the kinematic chain made use of by the containers.

One significant advantage of the previously described device consists of the fact that inside the pipetting area, the processor knows the exact position of the tubes and their identity. As a result, it is able to control the movements and functioning of the pipetting head, according to a programme independent of the order of the container being introduced into the robot but according to the nature and duration of the analyses, indeed even the urgency of the analysis.

Of course, the invention is not merely limited to the previously described embodiment.

Thus, the robot could include a direct access zone $ZE_3$ making it possible to have on the conveyor $CB_1$ a container not originating from the basket placed inside the distributor.

Similarly, it could include a trap TR situated at the level of the outlet zone $ZS_2$ making it possible to extract or have available a tube inside a container positioned in the zone $ZS_2$ for being sorted or selected.

We claim:

1. A method for analysing samples contained in recipients by means of an autoanalyser comprising a pipetting head movable along two perpendicular axis above a pipetting area containing said recipients disposed according to a matrix distribution, for injecting products or for taking samples in said recipients, said method comprising a preliminary phase of placing said recipient inside containers each having a longitudinal axis wherein said containers are vertically centred and disposed in line along said longitudinal axis and an operating cycle comprising the following phase, i. a first phase of moving successively said containers along a first rectilinear path to an access zone of said pipetting area, said containers being oriented parallel to said first path, ii. a second phase of identifying said recipients while said containers are moving along said first rectilinear path, iii. a third phase of moving step by step said containers along a second rectilinear path perpendicular to said first path wherein said containers are placed side by side, parallel to said first path and are moved in translation, iv. a fourth phase of moving said containers along a third rectilinear path parallel to said first path, said containers being oriented parallel to said first path, v. a fifth phase of moving step by step said container along a fourth rectilinear path parallel to the second path, ending in an outlet zone in said first path, said containers being side by side and axed parallel to said first path wherein at each step, the recipient of the containers present in the second and four paths are disposed in the pipetting area according to said matrix configuration, vi. a sixth phase of moving each of said containers along said first path so as to bring this container either to the first access zone and to restart said operating cycle or to a zone for evacuating this container.

2. Method according to claim 1, wherein before carrying out said first phase the said containers containing the recipients are arranged side by side in transportable baskets intended to be placed in a distributor which delivers the containers one by one.

3. Method according to claim 1, wherein the said second phase of identifying said recipients is carried out in a zone between said outlet zone and said access zone.

4. Method according to claim 1, wherein the sample recipients consists of cylindrical tubes each having a longitudinal axis of symmetry and wherein the said second phase of identifying said recipients comprises a step of rotating each tube about its longitudinal axis of symmetry and simultaneously a step of reading an identifying means provided on a cylindrical surface of said tube by an optoelectronic reading device.

5. An autoanalyzer for automatic analyzing samples contained in recipients disposed in containers having a longitudinal axis, said autoanalyzer comprising first and second parallel longitudinal conveyors transporting said containers in line with said longitudinal axis parallel to said conveyor and first and second parallel transversal conveyors axed perpendicular to said longitudinal conveyors and transporting said containers side by side, oriented parallel to said longitudinal conveyors, the containers present on said transversal conveyors defining a pipetting area inside which said recipients are arranged according to a matrix distribution and a pipetting head movable above said pipetting area along two perpendicular axis, each of said longitudinal conveyors being ended by two respective transfer zones so as to transfer said containers respectively on said transversal conveyors and said transversal conveyors being ended by two other transfer zones so as to transfer said containers on said longitudinal conveyors so that each of said containers is successively transported on said first longitudinal conveyor, on said first transversal conveyor, on said longitudinal conveyor and on said second transversal conveyor.

6. Autoanalyzer according to claim 5, which comprises a distributor delivering the said containers one by one providing from a basket on one of the two longitudinal conveyors.

7. Autoanalyzer according to claim 5, wherein the longitudinal conveyors are belt conveyors whose belts are fitted with notches.

8. Autoanalyzer according to claim 5, which includes a recipient identification station situated between one inlet zone and one outlet zone of the pipetting area provided on one of the longitudinal conveyors which is used as input conveyor.

9. Autoanalyzer according to claim 8, wherein said identification station includes on one side of said input conveyor an optoelectronic reading device, and on the other side a device for driving said recipients in rotation.

10. Autoanalyzer according to claim 9, wherein the input conveyor associated with the reading device includes upstream of this station a direct access zone of a container and/or a trap making it possible to extract or have available or extract one of said recipients in one of said containers located in said direct access zone.

11. An autoanalyzer for automatic analyzing samples contained in recipients disposed in containers having a longitudinal axis, said autoanalyser comprising first and second parallel longitudinal conveyors transporting said conveyors in line with said longitudinal axis parallel to said conveyor and first and second parallel transversal conveyors axed perpendicular to said longitudinal conveyors and transporting said containers side by side, with said longitudinal axis oriented parallel to said longitudinal conveyor, the containers present on said transversal conveyors defining a pipetting area inside which said recipients are arranged according to a matrix distribution and a pipetting head movable above said pipetting area along two perpendicular axis, each of said longitudinal conveyors being ended by two respective transfer zones so as to transfer said containers respectively on said transversal conveyors and said transversal conveyors being ended by two other transfer zones so as to transfer said containers on said longitudinal conveyors wherein said transversal conveyors comprising a guiding rail having an inverted $\Omega$ shape which cooperates with a T-shaped transversal prismatic cavity provided in the container, and two drive strips disposed and fitted on both sides of said guiding rail, said drive strips having notches whose pitch is approximately equal to the thickness of the containers.

12. An autoanalyzer for automatic analyzing samples contained in recipients disposed in containers having a longitudinal axis, said autoanalyser comprising first and second parallel longitudinal conveyors transporting said conveyors in line with said longitudinal axis parallel to said conveyor and first and second parallel transversal conveyors axed perpendicular to said longitudinal conveyors and transporting said containers side by side, with said longitudinal axis oriented parallel to said longitudinal conveyor, the containers present on said transversal conveyors defining a pipetting area inside which said recipients are arranged according to a matrix distribution and a pipetting head movable above said pipetting area along two perpendicular axis, each of said longitudinal conveyors being ended by two respective transfer zones so as to transfer said containers respectively on said transversal conveyors and said transversal conveyors being ended by two other transfer zones so as to transfer said containers on said longitudinal conveyors wherein said basket comprises a rail having a central part and two lateral wings, which cooperates with a T-shaped prismatic cavity provided said containers, said rail having a section comprising means for retracting said wings.

13. Autoanalyzer according to claim 12, wherein said rail includes a section with retractable wings.

* * * * *